(12) United States Patent
Manzo

(10) Patent No.: US 7,998,154 B2
(45) Date of Patent: Aug. 16, 2011

(54) METHOD AND APPARATUS FOR RADICAL PROSTATECTOMY ANASTOMOSIS

(75) Inventor: Scott E. Manzo, Shelton, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1127 days.

(21) Appl. No.: 10/514,140

(22) PCT Filed: Apr. 16, 2003

(86) PCT No.: PCT/US03/11916
§ 371 (c)(1),
(2), (4) Date: Nov. 9, 2004

(87) PCT Pub. No.: WO04/000137
PCT Pub. Date: Dec. 31, 2003

(65) Prior Publication Data
US 2005/0171564 A1   Aug. 4, 2005

Related U.S. Application Data

(60) Provisional application No. 60/390,104, filed on Jun. 19, 2002.

(51) Int. Cl.
*A61B 17/08* (2006.01)
*A61M 29/00* (2006.01)
(52) U.S. Cl. .................................... 606/153; 606/192
(58) Field of Classification Search .......... 606/192–194, 606/153–156; 623/1.15; 604/101.05, 103.07, 604/103.08
See application file for complete search history.

(56) References Cited

U.S. PATENT DOCUMENTS

| 2,127,903 | A |   | 8/1938  | Bowen                    |
|-----------|---|---|---------|--------------------------|
| 3,874,388 | A | * | 4/1975  | King et al. ...... 606/232 |
| 4,349,029 | A | * | 9/1982  | Mott ............. 604/103.07 |
| 4,553,543 | A |   | 11/1985 | Amarasinghe              |
| 4,803,984 | A |   | 2/1989  | Narayanan et al.         |
| 4,848,367 | A |   | 7/1989  | Avant et al.             |
| 4,911,164 | A |   | 3/1990  | Roth                     |
| 4,957,499 | A |   | 9/1990  | Lipatov et al.           |
| 5,002,558 | A | * | 3/1991  | Klein et al. ...... 606/192 |
| 5,047,039 | A |   | 9/1991  | Avant et al.             |
| 5,122,156 | A |   | 6/1992  | Granger et al.           |
| 5,146,925 | A | * | 9/1992  | Snow ............ 600/435  |
| 5,234,448 | A |   | 8/1993  | Wholey et al.            |

(Continued)

FOREIGN PATENT DOCUMENTS
WO    03/088848    10/2003
(Continued)

OTHER PUBLICATIONS

U.S. Appl. No. 10/516,47, entitled "Method and Apparatus for Anastomosis Including Annular Joining Member", filed Nov. 30, 2004.

(Continued)

*Primary Examiner* — Gary Jackson
*Assistant Examiner* — Katherine M Dowe

(57) ABSTRACT

Apparatus (100) for performing a surgical anastomosis include a tubular body (102) having an expandable anchor (114) operatively coupled near a distal end thereof. The apparatus further includes a sleeve (104) slidably received about the tubular body. The sleeve has an expandable anchor operatively coupled near a distal end thereof. The expandable anchor of the tubular body has an annular (116) ring concentric with a longitudinal axis defined by the tubular body.

17 Claims, 7 Drawing Sheets

U.S. PATENT DOCUMENTS

| | | | |
|---|---|---|---|
| 5,403,333 A | 4/1995 | Kaster et al. |
| 5,411,508 A | 5/1995 | Bessler et al. |
| 5,425,739 A | 6/1995 | Jessen |
| 5,464,414 A | 11/1995 | Cziffer |
| 5,464,415 A | 11/1995 | Chen |
| 5,478,353 A | 12/1995 | Yoon |
| 5,486,187 A | 1/1996 | Schenck |
| 5,540,701 A | 7/1996 | Sharkey et al. |
| 5,545,171 A | 8/1996 | Sharkey et al. |
| 5,549,619 A | 8/1996 | Peters et al. |
| 5,554,162 A | 9/1996 | DeLange |
| 5,569,272 A | 10/1996 | Reed et al. |
| 5,578,044 A | 11/1996 | Gordon et al. |
| 5,591,179 A | 1/1997 | Edelstein |
| 5,591,206 A | 1/1997 | Moufarrège |
| 5,695,504 A | 12/1997 | Gifford, III et al. |
| 5,700,272 A | 12/1997 | Gordon et al. |
| 5,702,412 A | 12/1997 | Popov et al. |
| 5,707,380 A | 1/1998 | Hinchliffe et al. |
| 5,713,889 A | 2/1998 | Chang |
| 5,716,370 A | 2/1998 | Williamson, IV et al. |
| 5,741,277 A | 4/1998 | Gordon et al. |
| 5,797,934 A | 8/1998 | Rygaard |
| 5,814,005 A | 9/1998 | Barra et al. |
| 5,817,113 A | 10/1998 | Gifford, III et al. |
| 5,833,698 A | 11/1998 | Hinchliffe et al. |
| 5,868,762 A | 2/1999 | Cragg et al. |
| 5,904,697 A | 5/1999 | Gifford, III et al. |
| 5,944,730 A | 8/1999 | Nobles et al. |
| 5,951,576 A | 9/1999 | Wakabayashi |
| 5,980,483 A | 11/1999 | Dimitri |
| 6,024,748 A | 2/2000 | Manzo et al. |
| 6,048,351 A | 4/2000 | Gordon et al. |
| 6,051,007 A | 4/2000 | Hogendijk et al. |
| 6,063,114 A | 5/2000 | Nash et al. |
| 6,080,167 A | 6/2000 | Lyell |
| 6,096,051 A | 8/2000 | Kortenbach et al. |
| 6,149,658 A | 11/2000 | Gardiner et al. |
| 6,152,937 A | 11/2000 | Peterson et al. |
| 6,171,319 B1 | 1/2001 | Nobles et al. |
| 6,171,321 B1 | 1/2001 | Gifford, III et al. |
| 6,176,864 B1 | 1/2001 | Chapman |
| 6,203,553 B1 | 3/2001 | Robertson et al. |
| 6,241,742 B1 | 6/2001 | Spence et al. |
| 6,245,083 B1 * | 6/2001 | Black et al. .................. 606/153 |
| 6,254,617 B1 | 7/2001 | Spence et al. |
| 6,280,460 B1 | 8/2001 | Bolduc et al. |
| 6,468,298 B1 * | 10/2002 | Pelton ........................ 623/1.11 |
| 7,056,323 B2 * | 6/2006 | Mareiro et al. ............... 606/108 |

FOREIGN PATENT DOCUMENTS

| | | |
|---|---|---|
| WO | 04/000093 | 12/2003 |
| WO | 04/000134 | 12/2003 |
| WO | 04/000135 | 12/2003 |
| WO | 04/000136 | 12/2003 |
| WO | 2004/098148 | 11/2004 |

OTHER PUBLICATIONS

U.S. Appl. No. 10/517,404, entitled "Method and Apparatus for Anastomosis Including an Anchoring Sleeve", filed Dec. 7, 2004.

U.S. Appl. No. 10/518,040, entitled "Method and Apparatus for Anastomosis Including Annular Adjoining Member", filed Dec. 9, 2004.

U.S. Appl. No. 10/514,774, entitled Method and Apparatus for Anastomosis Including an Anchoring Sleeve, filed Nov. 17, 2004.

U.S. Appl. No. 10/516,434, entitled "Method and Apparatus for Anastomosis", filed Nov. 30, 2004.

Internation Search Report for PCT/US03/11916 date of completion is Dec. 3, 2003 (3 pages).

* cited by examiner

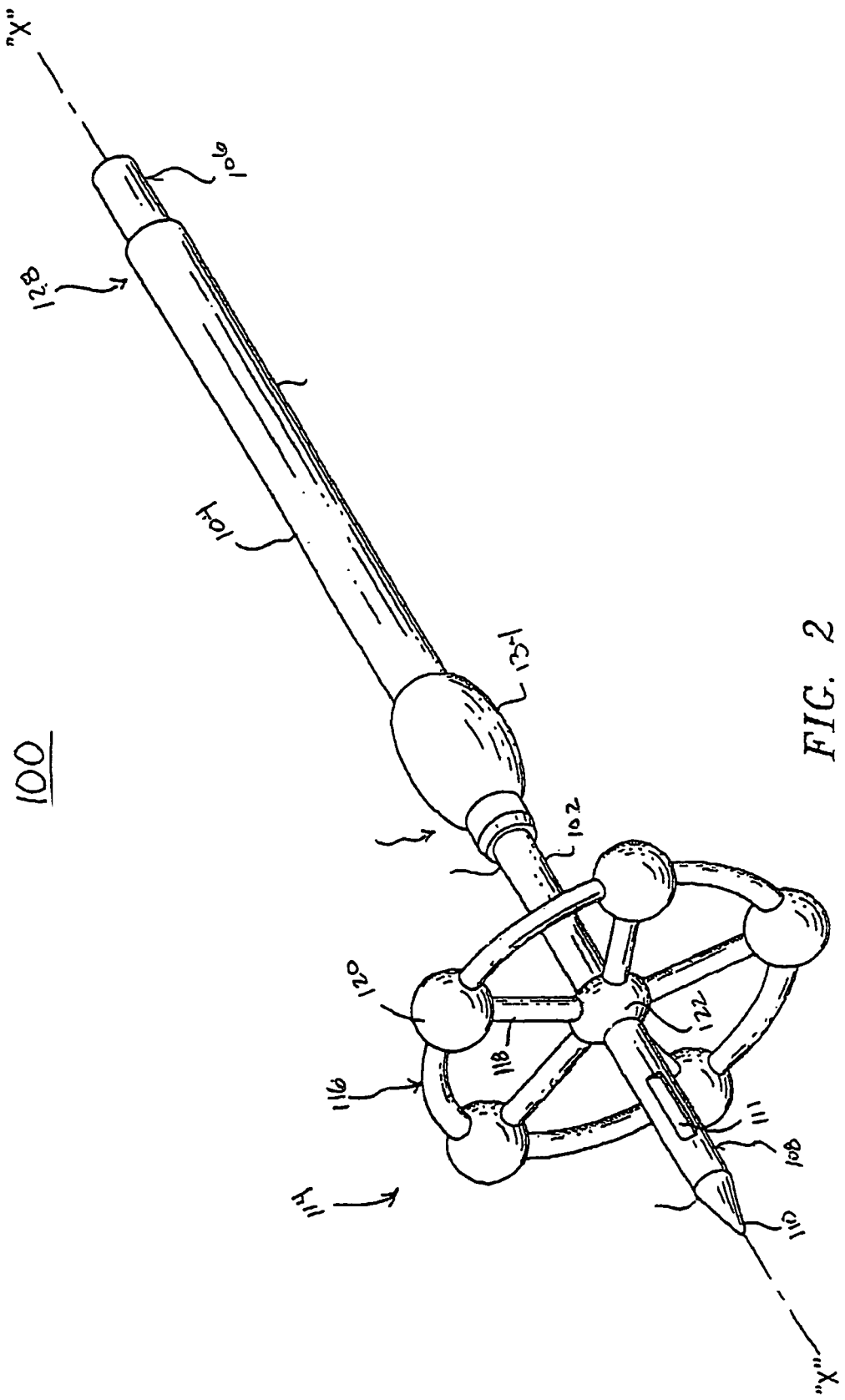

METHOD AND APPARATUS FOR RADICAL PROSTATECTOMY ANASTOMOSIS

CROSS REFERENCE TO RELATED APPLICATIONS

This is a National Stage Application of PCT/US 03/11916 under 35 USC §371(a), which claims priority of U.S. Provisional Patent Application Ser. No. 60/390,104 filed Jun. 19, 2002, the entire contents of which are hereby incorporated by reference.

BACKGROUND

1. Technical Field

The present disclosure relates to apparatus and methods for anastomosing two hollow body parts and, more particularly to apparatus and methods for anastomosing a urethral stump of a patient to the bladder following a radical prostatectomy.

2. Background of Related Art

Anastomosis is the bringing together and/or joining of two hollow or tubular structures. Most body conduits are generally cylindrical in configuration and have a circular cross-section. When it is desired to suture such a conduit, typically for attachment to another body conduit, sutures are placed around the circumference of the conduit in order to maintain the patency of its lumen or channel. This type of attachment is commonly referred to as an anastomosis. It can be appreciated that the sutures made on top of the conduit (i.e., on the side facing the surgeon) in an anastomosis are made relatively more easily than the sutures made underneath the conduit (i.e., on the side facing away from the surgeon).

The complexity of anastomosis attachment is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179, issued to Edelstein, there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164, issued to Roth, there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039, issued to Avant et al., there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using the prior art devices continues to be time consuming and to require great skill. Accordingly, the need exists for radical prostatectomy anastomosis devices which overcome the drawbacks of the prior art devices and which are quick and simple to use.

SUMMARY

Apparatus and methods for performing a surgical anastomotic procedure are disclosed herein. An apparatus for performing the surgical anastomosis includes a tubular body having a first expandable anchor operatively coupled near a distal end thereof, and a sleeve slidably received about the tubular body, the sleeve having a second expandable anchor operatively coupled near a distal end thereof. The first expandable anchor has a central hub, a plurality of spokes extending radially from the central hub and an annular ring interconnecting a distal end of each of the plurality of spokes. The central hub, spokes and annular ring define a cavity.

Preferably, the second expandable anchor has a first position in which the second expandable anchor is at most equal to the radius of the sleeve and a second position in which the second expandable anchor has a radius which is greater than the radius of the sleeve.

Preferably, the first expandable anchor has a first position in which the first expandable anchor has a radius which is at most equal to the radius of the tubular body and a second position in which the first expandable anchor has a radius which is greater than the radius of the tubular body.

In one preferred embodiment, the expandable anchor of the tubular body includes a spherical portion at the intersection of each of the plurality of spokes and the annular ring. The first expandable anchor is desirably inflatable. Preferably, the tubular body includes an inflation lumen in fluid communication with the cavity of the first expandable anchor. The inflation lumen is preferably configured and adapted to inject and withdraw a fluid into and out of the cavity of the expandable anchor of the tubular body in order to thereby inflate and deflate the expandable anchor of the tubular body. The tubular body desirably defines a lumen extending therethrough and includes an opening formed near a distal end thereof. Preferably, the opening is formed distally of the expandable anchor.

In accordance with certain embodiments, the second expandable anchor defines a cavity and the sleeve includes an inflation lumen in fluid communication with the cavity of the second expandable anchor. The inflation lumen is configured and adapted to inject and withdraw a fluid into and out of the cavity of the expandable anchor of the sleeve in order to inflate and deflate the expandable anchor of the sleeve. The expandable anchor of the sleeve may be substantially spherical when in an expanded condition. Other shapes are envisioned including but not limited to elliptical, cylindrical, etc.

In a further aspect of the present invention, an apparatus for performing a surgical anastomosis includes a tubular body having a first expandable anchor operatively coupled near a distal end thereof and defining a longitudinal axis. The apparatus has a sleeve slidably received about the tubular body, the sleeve having a second expandable anchor operatively coupled near a distal end thereof. The first expandable anchor has an annular concentric with the longitudinal axis.

In a preferred embodiment, the first expandable anchor includes a plurality of spokes attached to the annular ring and a spherical portion at the intersection of each of the plurality of spokes and the annular ring.

The first expandable anchor is desirably inflatable. Preferably, the tubular body includes an inflation lumen in fluid communication with the cavity of the first expandable anchor. The inflation lumen is preferably configured and adapted to inject and withdraw a fluid into and out of the cavity of the expandable anchor of the tubular body in order to thereby inflate and deflate the expandable anchor of the tubular body. The tubular body desirably defines a lumen extending therethrough and includes an opening formed near a distal end thereof. Preferably, the opening is formed distally of the expandable anchor.

In accordance with certain embodiments, the second expandable anchor defines a cavity and the sleeve includes an inflation lumen in fluid communication with the cavity of the second expandable anchor. The inflation lumen is configured and adapted to inject and withdraw a fluid into and out of the cavity of the expandable anchor of the sleeve in order to inflate and deflate the expandable anchor of the sleeve. The expandable anchor of the sleeve may be substantially spherical when in an expanded condition. Other shapes are envisioned including but not limited to elliptical, cylindrical, etc.

The second expandable anchor desirably comprises a sponge, or a plurality of flexible arms biased toward an expanded position.

In a further aspect of the present invention, a method for performing a surgical anastomotic procedure includes passing an apparatus through a first body vessel and into a second body vessel such that a first expandable anchor on a tubular body of the apparatus is positioned distally of the second body vessel. The first expandable anchor is expanded to engage the second body vessel. A sleeve of the apparatus is positioned such that a second expandable anchor on the sleeve is located near the first body vessel. The sleeve is slidably received around the tubular body. The second expandable anchor is expanded to engage the first body vessel. The tubular body is withdrawn until the second body vessel contacts a distal end of the first body vessel. The tubular body is fixed to the sleeve.

The tubular body may define a longitudinal axis and the first expandable anchor may comprise an annular ring concentric with the longitudinal axis. The step of expanding the first expandable anchor may comprise inflating the first expandable anchor so that the annular ring moves from a collapsed configuration to an expanded configuration encircling the longitudinal axis.

In one preferred embodiment, the apparatus is passed trans-urethrally through a urethra and a bladder neck into a bladder and the step of expanding the first expandable anchor includes engaging the bladder. The step of positioning the sleeve desirably includes positioning the second expandable anchor near the urethral stump.

In a preferred embodiment, the method includes removing the prostate gland, freeing the urethra from the prostate gland to thereby define a urethral stump, and freeing the prostate gland from the bladder to thereby define a bladder neck.

These and other advantages and features of the present apparatus and method disclosed herein, will become apparent through reference to the following description of embodiments, the accompanying drawings and claims.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

FIG. 2 is a perspective view of the apparatus of FIG. 1, shown in an anchoring condition;

DETAILED DESCRIPTION OF PREFERRED EMBODIMENTS

Figure 1:
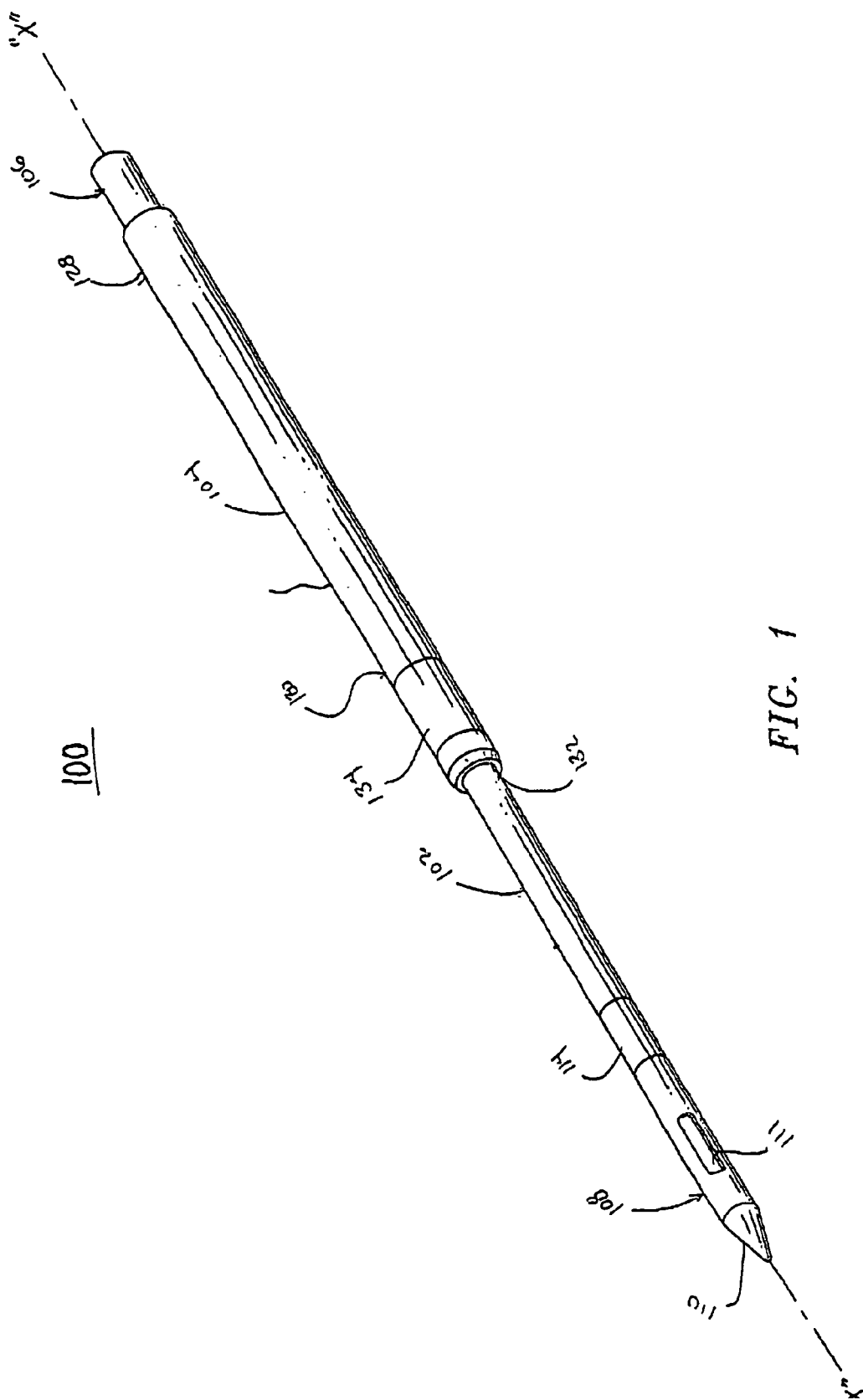
FIG. 1 is a perspective view of an apparatus for performing an anastomotic procedure, in accordance with an embodiment of the present disclosure, shown in an insertion or withdrawal condition.

Preferred embodiments of the presently disclosed apparatus for performing an anastomosis will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Referring to FIGS. 1-8, embodiments of anastomosis apparatus, in accordance with the principles of the present disclosure, are shown generally as reference numeral 100. Although apparatus 100 offers significant advantages to a radical prostatectomy procedure, it will be understood that the device is applicable for use in any anastomotic procedure where the end of a conduit is to be sutured or otherwise secured to a hollow body organ.

As seen in FIG. 1, apparatus 100 includes a tubular body 102 and a sleeve 104 slidably received about tubular body 102. Tubular body 102 includes a proximal end 106 and distal end 108, wherein distal end 108 is provided with a conical cap 110. Tubular body 102 includes at least one opening 111 formed near distal end 108 which opening 111 provided access to a central lumen 112 (see FIGS. 7A and 7B). Central lumen 112 of tubular body 102 defines a central longitudinal axis "X". Opening 111 and central lumen 112 function much like a Foley-type catheter and permit fluid to be drained from or infused into the target operative site and/or define an access channel through which optical instruments can be passed through in order to aid in the viewing of surrounding tissue.

Tubular body 102 further includes an expandable anchor 114 provided near distal end 108 of tubular body 102. Preferably, anchor 114 is located proximally of opening 111 and is configured and adapted to surround tubular body 102. Anchor 114 has a first retracted position in which axial movement of tubular body 102 through a body lumen is possible and a second expanded position (see FIGS. 2, 3 and 5-7B) in which axial movement of tubular body 102 through the body lumen is either restricted or prevented. In other words, anchor 114 has a first position in which anchor 114 has a radius which is substantially equal to or less than a radius of tubular body 102 and has a second position in which anchor 114 has a radius which is greater than the radius of tubular body 102.

Figure 3A:
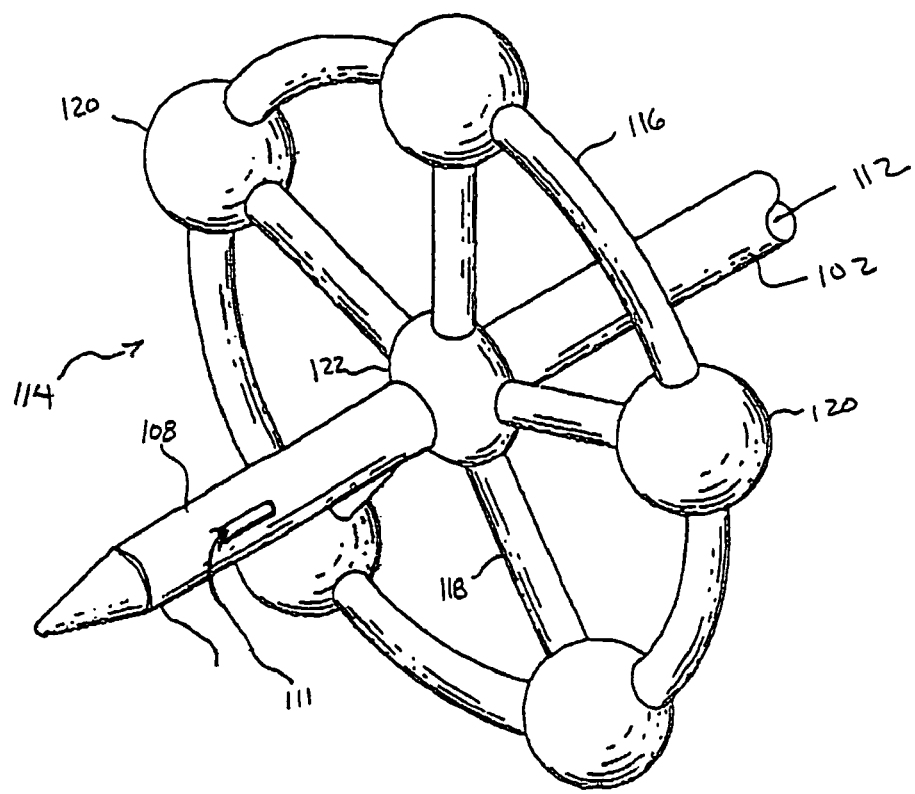
FIG. 3A is an enlarged perspective view of a distal end of the apparatus shown in FIG. 2.

In particular, as seen in FIGS. 2 and 3A, expandable anchor 114 is preferably fabricated of an expandable material and preferably forms a circular or "wagon wheel" shaped structure. Anchor 114 includes a plurality of arcuate members 116 defining a ring, a plurality of spokes 118 and a bulbous or spherical portion 120 provided at the intersection of arcuate members 116 with each spoke 118. Preferably, spokes 118 unite at a central bulbous or spherical hub 122. Central hub 122, spokes 118, spherical portions 120 and arcuate members 116 define a single inflatable cavity 117 (see FIG. 7B). While a single cavity 117 has been described, it is envisioned that a plurality of discrete cavities can be formed which discrete cavities can be concomitantly or separately inflated or expanded.

While a plurality of spokes 118 have been disclosed, it is envisioned that an annular disc-like member can be provided to interconnect central hub 122 to the plurality of spherical portions 120 and that a single lumen can extend between central hub 122 and each spherical portion 120. While a "wagon wheel" like expandable anchor 114 is preferred, it is envisioned that expandable anchor 114 can take any geometric shape, depending on its particular application, and could include such forms as an oval or spiral, for example.

In the preferred embodiment, tubular body 102 is provided with a first inflation/deflation lumen 124 (see FIG. 7B) extending along the wall of central lumen 112 and is in fluid communication with inflatable cavity 117 of expandable anchor 114 through at least one access opening 126 formed in tubular body 102. In use, lumen 124 is coupled to a source of inflation fluid (not shown) and a fluid is injected through inflation/deflation lumen 124 in order to inflate and expand anchor 114 to a deployed condition. Concomitantly, withdrawal of the fluid used to inflate and expand anchor 114 will cause anchor 114 to deflate and retract.

A "wagon wheel" expandable anchor 114 having spherical portions 120 and a spherical hub 122 is preferred in order to reduce the contact points of anchor 114 with the body tissue thereby reducing the tendency of tissue to be injured (e.g., ischemia) as a result of the anastomotic apparatus remaining within a body vessel and in contact with the surrounding body tissue for an extended period of time. In other words, spherical portions 120 and spherical hub 122 minimize the amount of direct contact between the body vessel, i.e., the bladder wall, and expandable anchor 114. In use, it is envisioned that expandable anchor 114 can be partially deflated, translated, readily repositioned radially within the bladder and re-inflated as needed.

Returning to FIG. 1, sleeve 104 includes a proximal end 128 and a distal end 130 defining a lumen 132 extending therethrough. Distal end 130 of sleeve 104 is preferably tapered in order to facilitate passage of sleeve 104 through a body lumen. In accordance with the present disclosure, sleeve 104 includes an expandable cuff 134 provided near a distal end thereof. Preferably, expandable cuff 134 has a first position in which expandable cuff 134 has a radius which is less than or equal to a radius of sleeve 104 and a second position in which expandable cuff 134 has a radius which is greater than the radius of sleeve 104.

Figure 7A:
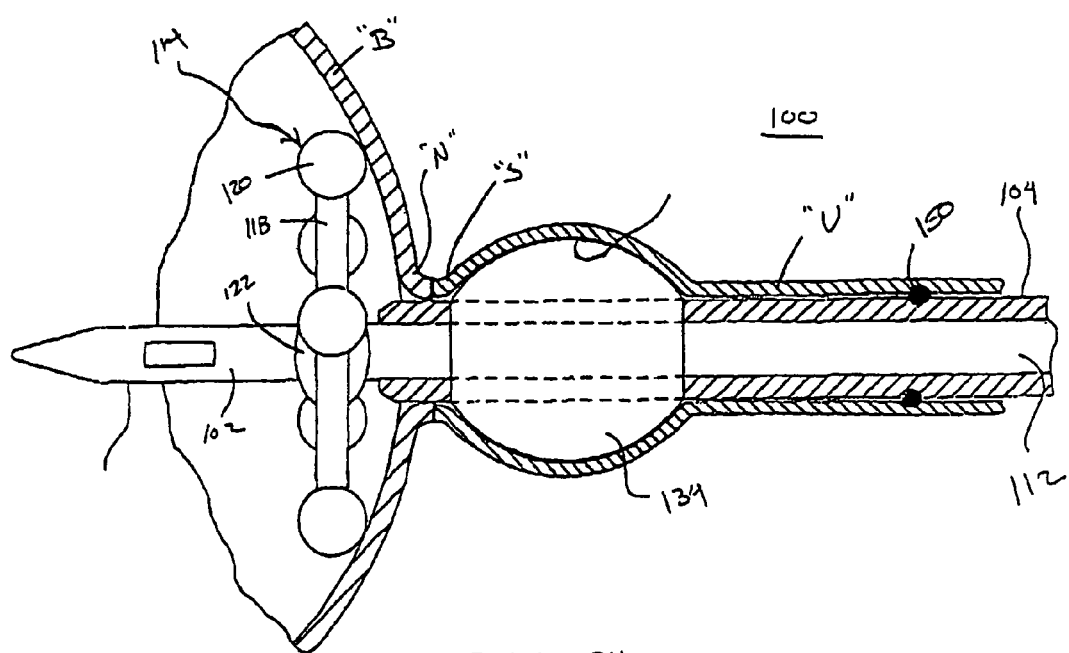
FIG. 7A is a partial cross-sectional side elevational view of a portion of the urinary system illustrating the bladder approximated to the urethra.
Figure 7B:
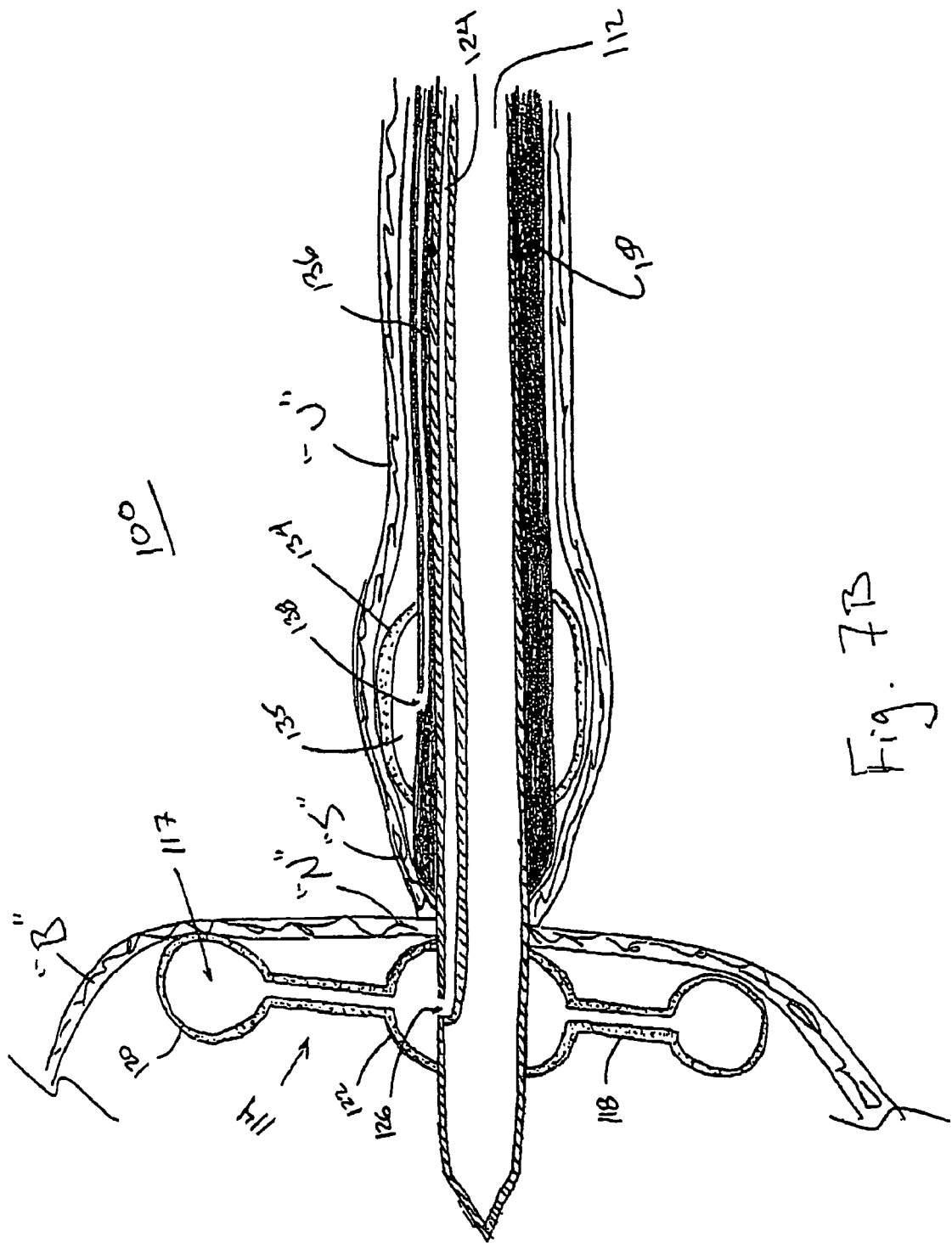
FIG. 7B is a cross-sectional side elevational view, taken along the longitudinal axis, of a portion of the urinary system illustrating the bladder approximated to the urethra.

As seen in FIG. 7B, sleeve 104 is provided with an inflation/deflation lumen 136 extending along the length thereof and is in fluid communication with expandable cuff 134 through at least one access opening 138 formed in sleeve 104. In use, lumen 136 is coupled to a source of inflation fluid (not shown) and a fluid is injected through inflation/deflation lumen 136 in order to inflate and expand cuff 134 to an expanded condition in order to anchor sleeve 104 within a body lumen. Concomitantly, withdrawal of the fluid used to inflate and expand cuff 134 will cause cuff 134 to deflate in order for sleeve 104 to be withdrawn from the body lumen.

Expandable anchor 114 and expandable cuff 134 are preferably fabricated from a medical grade polymer having suitable flexibility and structural integrity to withstand the forces associated with the inflation of anchor 114 and cuff 134 and with the function of anchoring apparatus 100 in place within a lumen of the patient's body.

It is contemplated that at least one annular seal, i.e., an O-ring, 150 (see FIGS. 7A and 7B) be provided between tubular body 102 and sleeve 104. Accordingly, it is envisioned that the annular seal prevents or reduces the possibility of fluids from passing between tubular body 102 and sleeve 104.

Figure 3B:
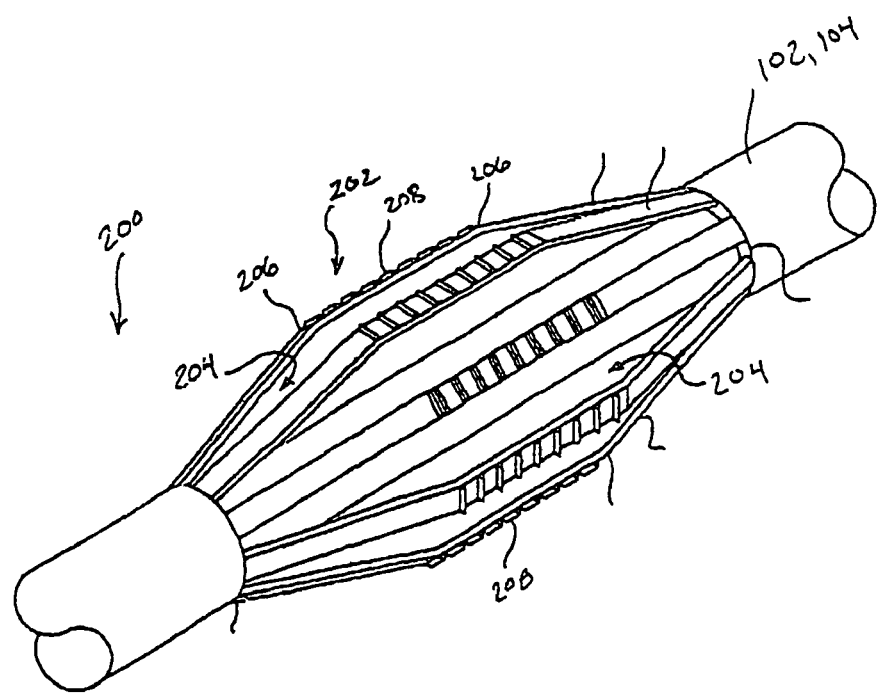
FIG. 3B is an enlarged perspective view of an anchoring mechanism in accordance with an alternative embodiment of the present disclosure.

Turning now to FIG. 3B, an alternative embodiment of an anchoring mechanism, in accordance with the present disclosure, is shown generally as reference numeral 200. Anchoring mechanism 200 includes at least a pair of retractable and expandable segments 202 formed in either tubular body 102 and/or sleeve 104. Segments 202 define at least a pair of slots 204. Preferably, anchor mechanism 200 includes eight expandable and retractable segments 202 separated by a respective number of slots 204. Each segment 202 is provided with a series of fold lines 206 located at specific locations and sides of each segment 202. The location and side of placement of fold lines 206 will cause anchor mechanism 200 to deform upon compression and extension of tubular body 102 or sleeve 104. Preferably, the location and side of placement of fold lines 206 will result in segments 202 of anchor mechanism 200 to expand radially outward upon compression of tubular body 102 or sleeve 104.

It is envisioned that each segment 202 is provided with a friction or grip enhancing coating or surface structure 208 which aides in securing segments 202 against body tissue and aides in controlling the movement of a body lumen, i.e., the urethra, when anchor mechanism 200 is deployed. In addition, surface structure 208 reduces the amount of surface which is in contact between segments 202 and the body tissue thereby reducing the risk of tissue damage, i.e., ischemia, by allowing for the areas of contact to be changed by adjusting the pressure or degree of expansion of anchor mechanism 200 and rotating tubular body 102 or sleeve 104 about central longitudinal axis "X".

In accordance with the principles of the present disclosure, it is envisioned that expandable anchor 114 and expandable cuff 134 can each be replaced with an anchoring mechanism similar to anchoring mechanism 200 formed along sleeve 104.

Various different materials may be used for expandable anchor 114 and expandable cuff 134 according to the present invention. Expandable anchor 114 and expandable cuff 134 should preferably be made of materials having acceptable properties including biocompatibility, pull strength, longitudinal or column strength, and bending flexibility. Some of the preferred materials may include various plastics, referred to as polymers, including nylon, polyethylenes, polyurethanes, or PET.

It is further contemplated that apparatus 100 include a locking mechanism for securing tubular body 102 to sleeve 104 and to prevent their relative axial movement with respect to one another.

A preferred method of use and operation of anastomosis apparatus 100 in a radical anastomotic procedure will now be described in greater detail with reference to FIGS. 1-8 and in particular with reference to FIGS. 4-8. Apparatus 100 can be used in either the retropubic or the perineal prostatectomy approaches. With the prostate removed, the bladder neck "N" of the bladder "B" is first reconstructed by everting the inner mucosal lining of bladder "B" and suturing it down to the outer wall of bladder "B" using known surgical techniques.

Likewise, urethral stump "S" of urethra "U" is reconstructed by everting the inner mucosal lining of urethral stump "S" and suturing it down to the outer wall of urethra "U", using known surgical techniques.

Preferably, with bladder neck "N" reconstructed, bladder neck "N" is sized to properly accommodate and retain distal end 108 of tubular body 102 within bladder "B" using a standard tennis racket type closure (i.e., the opening of the bladder neck constituting the head of the tennis racket and a radial incision extending from the bladder neck constituting the handle portion of the tennis racket. Most preferably, bladder neck "N" is sized to be approximately 7-8 mm in diameter.

Figure 4:
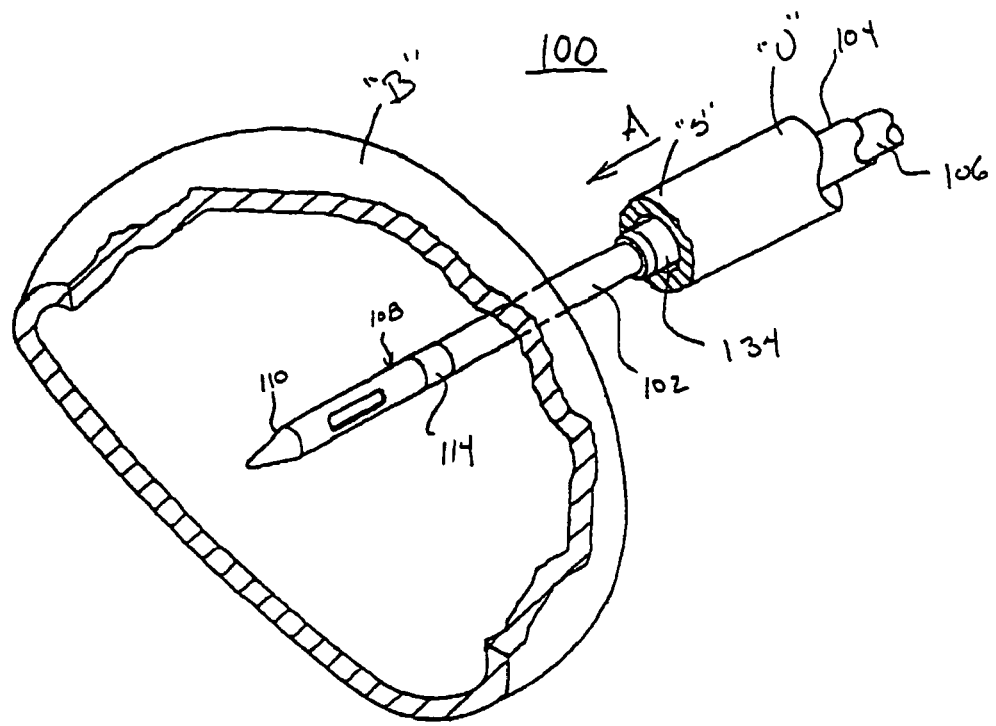
FIG. 4 is a partial cross-sectional view of a portion of a urinary system illustrating the insertion of the apparatus as shown in FIG. 1 into the surgical site.

With bladder neck "N" reconstructed, apparatus 100, including tubular body 102 and sleeve 104, is passed transurethrally through urethra "U" until distal end 108 of tubular body 102 extends out of urethral stump "S" and into bladder "B" through bladder neck "N", as indicated by arrow "A" in FIG. 4. In particular, distal end 108 of tubular body 102 is preferably positioned such that expandable anchor 114 of tubular body 102 is positioned entirely within bladder "B". In addition, distal end 130 of sleeve 104 is preferably positioned such that expandable cuff 134 is positioned near urethral stump "S" of urethra "U".

Figure 5:
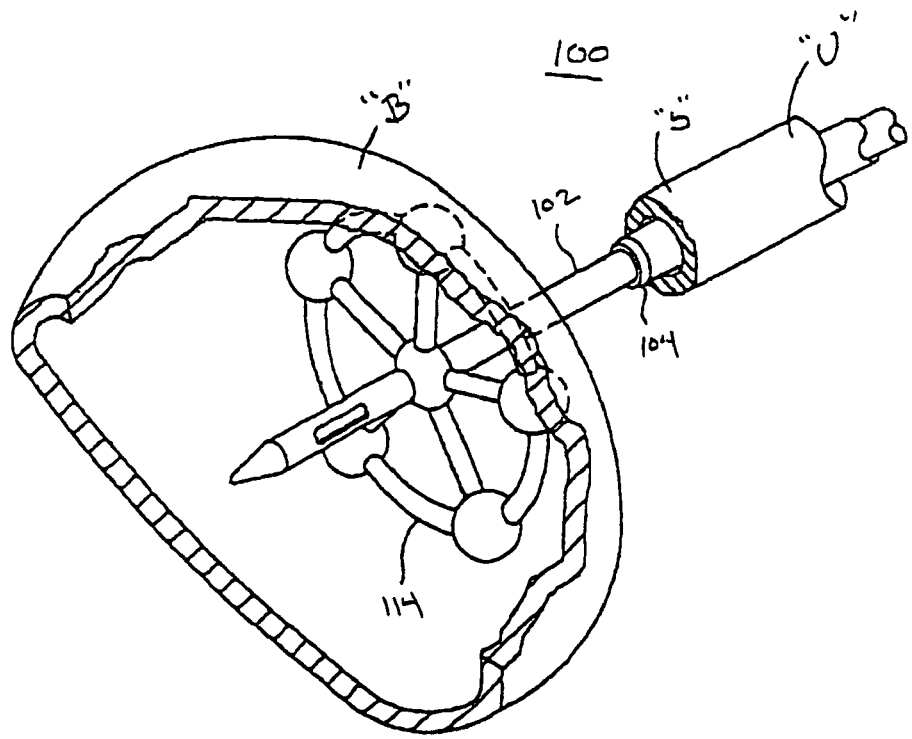
FIG. 5 is a partial cross-sectional view of a portion of the urinary system illustrating the apparatus as shown in FIG. 2, while in the operative site.
Figure 6:
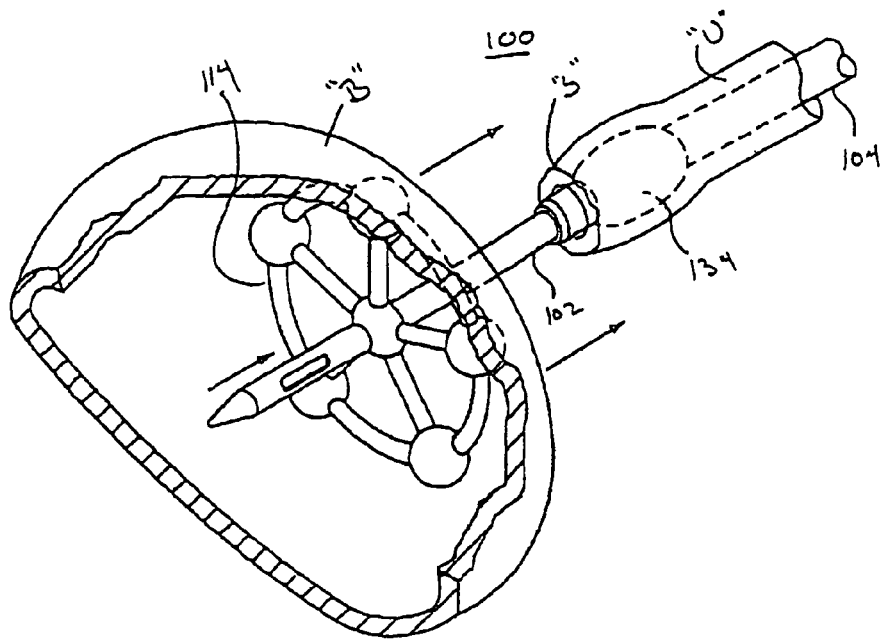
FIG. 6 is a partial cross-sectional view of a portion of the urinary system illustrating the approximation of the bladder to the urethra using the apparatus disclosed herein.

With tubular body 102 positioned within bladder "B", as seen in FIG. 5, a fluid, i.e., air, carbon dioxide, saline or the like, is introduced through lumen 124 into cavity 117 of anchor 114 to thereby expand and inflate anchor 114. Inflation and expansion of anchor 114 will prevent tubular body 102 from being withdrawn from bladder "B". As seen in FIG. 6, with sleeve 104 positioned near urethral stump "S", a fluid, i.e., air, carbon dioxide, saline or the like, is introduced through lumen 136 into cuff 134 to thereby expand and inflate cuff 134. Inflation of cavity 135 of cuff 134 results in the radial expansion of cuff 134 and in turn the pressing of cuff 134 against the inner surface of urethra "U" (see FIGS. 7A and 7B), thus preventing axial movement of sleeve 104 through urethra "U".

With both anchor 114 and cuff 134 in an expanded condition, tubular body 102 is withdrawn through sleeve 104 in a direction "D" as seen in FIG. 6. As tubular body 102 is withdrawn through sleeve 104 in direction "D", bladder "B" is also moved in direction "D" and approximated with urethral stump "S". Once bladder "B" has been approximated to urethral stump "S", tubular body 102 is locked in position relative to sleeve 104 thereby maintaining bladder "B" approximated with urethra "U".

With tubular body 102 and sleeve 104 anchored in place, opening 111 and central lumen 112 of tubular body 102 act like a Foley-type catheter to create a passage through which urine can be passed from bladder "B" and out through urethra "U".

Figure 8:
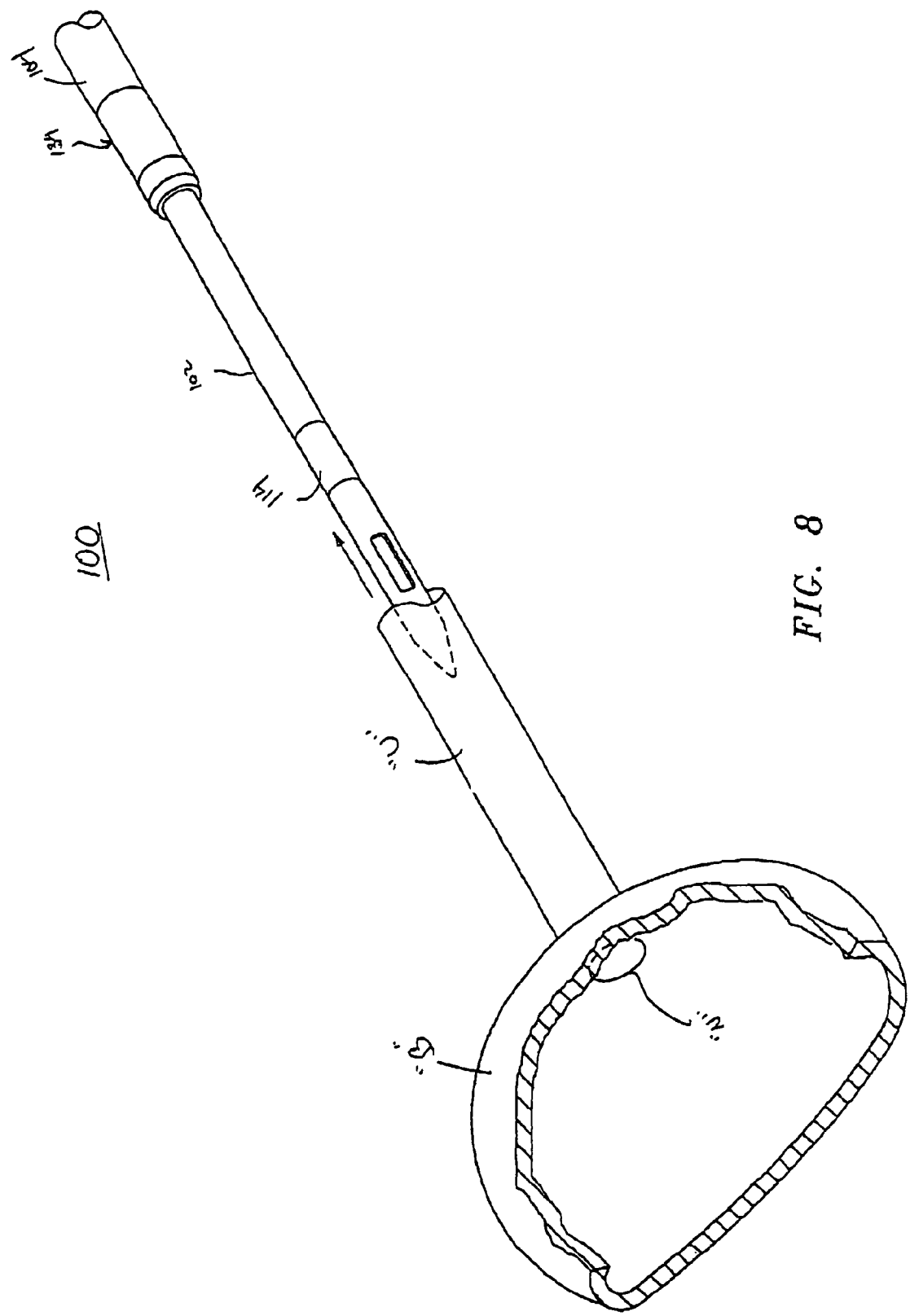
FIG. 8 is a partial cross-sectional view of a portion of the urinary system illustrating the withdrawal of the apparatus, as shown in FIG. 1, from the bladder and urethra while the apparatus is in the withdrawal condition.

In accordance with the present disclosure, it is preferred that tubular body 102 and sleeve 104 are maintained within bladder "B" and urethra "U" for a period of several weeks or for a period of time sufficient for bladder neck "N" and urethral stump "S" to heal and "grow" together. Once bladder neck "N" and urethral stump "S" have sufficiently healed, anchor 114 and cuff 134 are deflated and apparatus 100, including tubular body 102 and sleeve 104, is withdrawn from urethra "U", as seen in FIG. 8.

The expandable anchor for engaging a body vessel may comprise any expandable structure, including those disclosed in certain embodiments of the following PCT Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Radical Prostatectomy Anastomosis Including An Anchor For Engaging A Body Vessel And Deployable Sutures, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Expandable Member, invented by Russell Heinrich and Scott Manzo; Method And Apparatus For Anastomosis Including An Anchoring Sleeve, invented by Scott Manzo; Method and Apparatus for Radical Prostatectomy Anastomosis, invented by Scott Manzo; the disclosures of which are all hereby incorporated by reference herein, in their entirety.

The joining member for joining body vessels may comprise any joining member, including those disclosed in certain embodiments of the following PCT Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including An Anchor For Engaging A Body Vessel And Deployable Sutures, invented by Scott Manzo; Method And Apparatus For Radical Prostatectomy Anastomosis Including An Anchor For Engaging A Body Vessel And Deployable Sutures, invented by Scott Manzo; Method And Apparatus For Anastomosis Including An Anchoring Sleeve, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Expandable Member, invented by Russell Heinrich and Scott Manzo; Method And Apparatus For Anastomosis Including An Anchoring Sleeve, invented by Scott Manzo; Method and Apparatus for Radical Prostatectomy Anastomosis, invented by Scott Manzo; the disclosures of which are all hereby incorporated by reference herein, in their entirety.

The methods and apparatus disclosed herein may be used for approximating and/or joining the urethra and bladder, intestinal portions of the body, blood vessels or any other body vessels.

While apparatus in accordance with the present disclosure have been described as being used in connection with a radical prostatectomy procedure, it is envisioned that apparatus having similar structures and modes of operation can be used in various other surgical procedures. It will be understood that various modifications may be made to the embodiments of the presently disclosed anastomosis device and method disclosed herein.

In accordance with the principles of the present disclosure, it is envisioned that the apparatus has a tubular body including a proximal and a distal expandable anchor operatively coupled near a distal end thereof. Accordingly, in use, it is envisioned that the distal end of the tubular body is inserted into the bladder trans-urethrally until the distal expandable anchor is within the bladder, the distal anchor is expanded within the bladder, the tubular body is withdrawn through the urethra until the bladder neck contacts the urethral stump and the proximal anchor is expanded thereby anchoring the tubular body against the inner wall of the urethra.

Therefore, the above description should not be construed as limiting, but merely as an exemplification of a preferred embodiment. Those skilled in the art will envision other modifications within the scope of the present disclosure.

What is claimed is:

1. An apparatus for performing a surgical anastomosis, comprising:
    a tubular body defining a longitudinal axis therethrough, the tubular body having a first expandable anchor operatively coupled near a distal end thereof; and
    a sleeve slidably received about the tubular body, the sleeve having a second expandable anchor operatively coupled near a distal end thereof;
    the first expandable anchor including a central hub, a plurality of spokes extending radially from the central hub, an annular ring interconnecting a distal end of each of the plurality of spokes and at least one contact portion protruding from the annular ring at the intersection of each of the plurality of spokes and the annular ring in a direction substantially parallel to the longitudinal axis, wherein the central hub, the plurality of spokes and the annular ring define a cavity.

2. The apparatus of claim 1, wherein the first expandable anchor has a first position in which the first expandable anchor has a radius which is at most equal to the radius of the tubular body and a second position in which the first expandable anchor has a radius which is greater than the radius of the tubular body.

3. The apparatus of claim 1, wherein the second expandable anchor has a first position in which the second expandable anchor is at most equal to the radius of the sleeve and a second position in which the second expandable anchor has a radius which is greater than the radius of the sleeve.

4. The apparatus of claim 1, wherein the at least one contact portion includes a spherical portion portion has a radial diameter that is greater than a radial diameter of the annular ring.

5. The apparatus of claim 1, wherein the first expandable anchor is inflatable, the tubular body including an inflation lumen in fluid communication with the cavity of the expandable anchor of the tubular body.

6. The apparatus of claim 1, wherein the tubular body defines a lumen extending therethrough and includes an opening formed near a distal end thereof.

7. The apparatus of claim 1, wherein the second expandable anchor defines a cavity and the sleeve includes an inflation lumen in fluid communication with the cavity of the second expandable anchor.

8. An apparatus for performing a surgical anastomosis, comprising:
    a tubular body having a first expandable anchor operatively coupled near a distal end thereof and defining a longitudinal axis; and
    a sleeve slidably received about the tubular body, the sleeve having a second expandable anchor operatively coupled near a distal end thereof;
    the first expandable anchor including an annular ring concentric with the longitudinal axis, the annular ring defined by a plurality of discrete members radially spaced around the annular ring, a plurality of spokes attached to the annular ring and at least one contact portion protruding from the annular ring at the intersection of each of the plurality of spokes and the annular ring.

9. The apparatus of claim 8, wherein includes a the at least one contact portion includes a spherical portion spherical portion has a radial diameter that is greater than a radial diameter of the annular ring.

10. The apparatus of claim 8, wherein the first expandable anchor is inflatable, the tubular body including an inflation lumen in fluid communication with the cavity of the expandable anchor of the tubular body.

11. The apparatus of claim 8, wherein the tubular body defines a lumen extending therethrough and includes an opening formed near a distal end thereof.

12. The apparatus of claim 8, wherein the second expandable anchor defines a cavity and the sleeve includes an inflation lumen in fluid communication with the cavity of the second expandable anchor.

13. The apparatus of claim 8, wherein the second expandable anchor comprises an expandable anchor selected from the group consisting of: a sponge and a plurality of flexible arms biased toward an expanded position.

14. A method for performing a radical prostatectomy anastomosis, the method comprising the steps of:
providing an apparatus comprising a tubular body defining a longitudinal axis therethrough, the tubular body having a first inflatable anchor operatively coupled near a distal end thereof; and a sleeve slidably received about the tubular body, the sleeve having a second inflatable anchor operatively coupled near a distal end thereof; the first inflatable anchor including a central hub, a plurality of spokes extending radially from the central hub, an annular ring interconnecting a distal end of each of the plurality of spokes and at least one contact portion protruding from the annular ring at the intersection of each of the plurality of spokes and the annular ring in a direction substantially parallel to the longitudinal axis, wherein the central hub, the plurality of spokes and the annular ring define a cavity;
passing the apparatus through a urethra and into a bladder such that the first inflatable anchor on the tubular body of the apparatus is positioned distally of the bladder;
inflating the first inflatable anchor of the tubular body to engage the bladder;
positioning the sleeve of the apparatus so that the second inflatable anchor on the sleeve is located near the urethra;
inflating the second inflatable anchor of the sleeve to engage the urethra;
withdrawing the tubular body until the bladder contacts a distal end of the urethra; and
fixing the tubular body relative to the sleeve.

15. The method of claim 14, further comprising the step of removing a prostate gland by freeing the urethra from the prostate gland to thereby define a urethral stump, and freeing the prostate gland from the bladder to thereby define a bladder neck.

16. The method of claim 15, further comprising the step of maintaining the tubular body and sleeve within the bladder and urethra for a period of time sufficient for the bladder neck and urethral stump to heal and grow together.

17. The method according to claim 14, further comprising the step of draining fluid from the bladder through an opening that provides access to a central lumen in the tubular body.

* * * * *